United States Patent
Tan et al.

(10) Patent No.: US 10,111,610 B2
(45) Date of Patent: Oct. 30, 2018

(54) MICROSCALE PLASMA SEPARATOR

(71) Applicant: Wainamics, Inc., Fremont, CA (US)

(72) Inventors: Ming Tan, Danville, CA (US); Frank Zaugg, Redwood City, CA (US); Peter Kernen, Redwood City, CA (US)

(73) Assignee: Wainamics, Inc., Pleasanton, CA (US)

( * ) Notice: Subject to any disclaimer, the term of this patent is extended or adjusted under 35 U.S.C. 154(b) by 0 days.

(21) Appl. No.: 15/521,221

(22) PCT Filed: Nov. 3, 2015

(86) PCT No.: PCT/US2015/058731
§ 371 (c)(1),
(2) Date: Apr. 21, 2017

(87) PCT Pub. No.: WO2016/073415
PCT Pub. Date: May 12, 2016

(65) Prior Publication Data
US 2017/0354361 A1 Dec. 14, 2017

Related U.S. Application Data

(60) Provisional application No. 62/200,572, filed on Aug. 3, 2015, provisional application No. 62/074,713, filed on Nov. 4, 2014.

(51) Int. Cl.
*G01N 1/00* (2006.01)
*A61B 5/15* (2006.01)
(Continued)

(52) U.S. Cl.
CPC .. *A61B 5/150022* (2013.01); *A61B 5/150221* (2013.01); *A61B 5/150236* (2013.01);
(Continued)

(58) Field of Classification Search
CPC .................................................. B01D 33/00
See application file for complete search history.

(56) References Cited

U.S. PATENT DOCUMENTS

| | | | |
|---|---|---|---|
| 4,057,499 A | * | 11/1977 | Buono .................. B01D 33/01 210/136 |
| 4,477,575 A | | 10/1984 | Vogel |

(Continued)

FOREIGN PATENT DOCUMENTS

| | | |
|---|---|---|
| WO | WO2010/111086 | 9/2010 |
| WO | WO2014/023761 | 2/2014 |

(Continued)

OTHER PUBLICATIONS

Becker et al, "Highly efficient on-chip plasma/serum generation for disposable point-of-care devices," 14th International Conference on Miniaturized Systems for Chemistry and Life Sciences, Groningen, The Netherlands (Oct. 3-7, 2010).

(Continued)

*Primary Examiner* — Jyoti Nagpaul
(74) *Attorney, Agent, or Firm* — Stephen C. Macevicz

(57) ABSTRACT

The invention is directed to methods and devices for efficient separation of plasma irons whole blood which are suitable for point of care use in resource poor environments, in some embodiments, elements of such devices comprise (a) a sample collection receptacle (SCR) with at least one port, the sample collection receptacle capable of holding a predetermined volume of a sample of undiluted whole blood drawn through a port; (b) a filter chamber having an inlet and an outlet, and containing at least one filter capable of separating plasma from blood cells as sample passes from an inlet side to an outlet side of the at least one filter whenever the filter chamber is placed in Quid communication with a port of the sample collection receptacle; and (c) a manually driven pump operationally associated with the SCR and
(Continued)

filter chamber for (i) drawing a predetermined volume of sample into ore SCR by a first user action and (ii) driving the predetermined volume at a substantially constant linear flow under a pressure not exceeding 2 psi from the SCR through the filter chamber and the outlet of the filter chamber by a second user action.

6 Claims, 11 Drawing Sheets

(51) Int. Cl.
| | |
|---|---|
| *A61M 1/34* | (2006.01) |
| *G01N 33/49* | (2006.01) |
| *A61J 1/05* | (2006.01) |
| *B01L 3/02* | (2006.01) |
| *B01L 3/00* | (2006.01) |
| *A61J 1/06* | (2006.01) |

(52) U.S. Cl.
CPC .. *A61B 5/150244* (2013.01); *A61B 5/150343* (2013.01); *A61J 1/05* (2013.01); *A61J 1/06* (2013.01); *A61M 1/34* (2013.01); *A61M 1/3403* (2014.02); *A61M 1/3496* (2013.01); *B01L 3/0217* (2013.01); *B01L 3/502* (2013.01); *G01N 33/491* (2013.01); *A61M 2205/3331* (2013.01); *B01L 2200/0605* (2013.01); *B01L 2200/10* (2013.01); *B01L 2300/0681* (2013.01); *B01L 2300/0832* (2013.01)

(56) References Cited

U.S. PATENT DOCUMENTS

| | | | |
|---|---|---|---|
| 4,933,092 A | 6/1990 | Aunet | |
| 4,987,085 A | 1/1991 | Allen | |
| 5,110,724 A | 5/1992 | Hewett | |
| 5,262,067 A | 11/1993 | Wilk | |
| 5,728,306 A | 5/1998 | Breillatt | |
| 5,766,552 A | 6/1998 | Doshi | |
| 5,798,272 A | 8/1998 | Allen | |
| 5,895,575 A | 4/1999 | Kraus | |
| 5,996,811 A | 12/1999 | Kitajima | |
| 6,197,598 B1 | 3/2001 | Schrier | |
| 7,159,474 B2 | 1/2007 | Arabian | |
| 7,374,724 B2* | 5/2008 | Ingenhoven | B01L 3/0275 210/198.2 |
| 7,404,931 B2 | 7/2008 | Frey | |
| 7,713,232 B2* | 5/2010 | Uber, III | A61M 5/142 422/537 |
| 8,057,672 B2 | 11/2011 | Chung | |
| 8,470,259 B2 | 6/2013 | Gupta | |
| 8,889,071 B2 | 11/2014 | Aota | |
| 8,974,362 B2* | 3/2015 | Nash | B01D 21/262 494/37 |
| 8,999,161 B2 | 4/2015 | Mathias | |
| 2003/0206828 A1 | 11/2003 | Bell | |
| 2005/0101979 A1 | 5/2005 | Alden | |
| 2006/0207937 A1 | 9/2006 | Bonaguidi | |
| 2008/0128341 A1 | 6/2008 | Jang | |
| 2010/0093551 A1 | 4/2010 | Montagu | |
| 2012/0024788 A1 | 2/2012 | Kelso | |
| 2014/0263059 A1 | 9/2014 | Burg | |
| 2015/0125882 A1 | 5/2015 | Bornheimer | |

FOREIGN PATENT DOCUMENTS

| | | |
|---|---|---|
| WO | WO2014/172234 | 10/2014 |
| WO | WO2016/073415 | 2/2016 |
| WO | WO2016/073415 | 5/2016 |

OTHER PUBLICATIONS

Gong et al, "Field tested millimeter-scale blood filtration device for point-of-care applications," Biomicrofluidics, 7: 044111 (2013).

Haeberle et al, "Microfluidic platforms for lab-on-a-chip applications," LabChip, 7: 1094-1110 (2007).

Homsy et al, "Development and validation of a low cost blood filtration element separating plasma from undiluted whole blood," Biomicrofluidics, 6: 012504 (2012).

Moscovici et al, "Electrical power free, low dead volume, pressure-driven pumping for microfluidic applications," Biomicrofluidics, 4: 046501 (2010).

Toner et al, "Blood-on-a-chip," Annu. Rev Biomed. Eng., 7:77-103 (2005).

\* cited by examiner

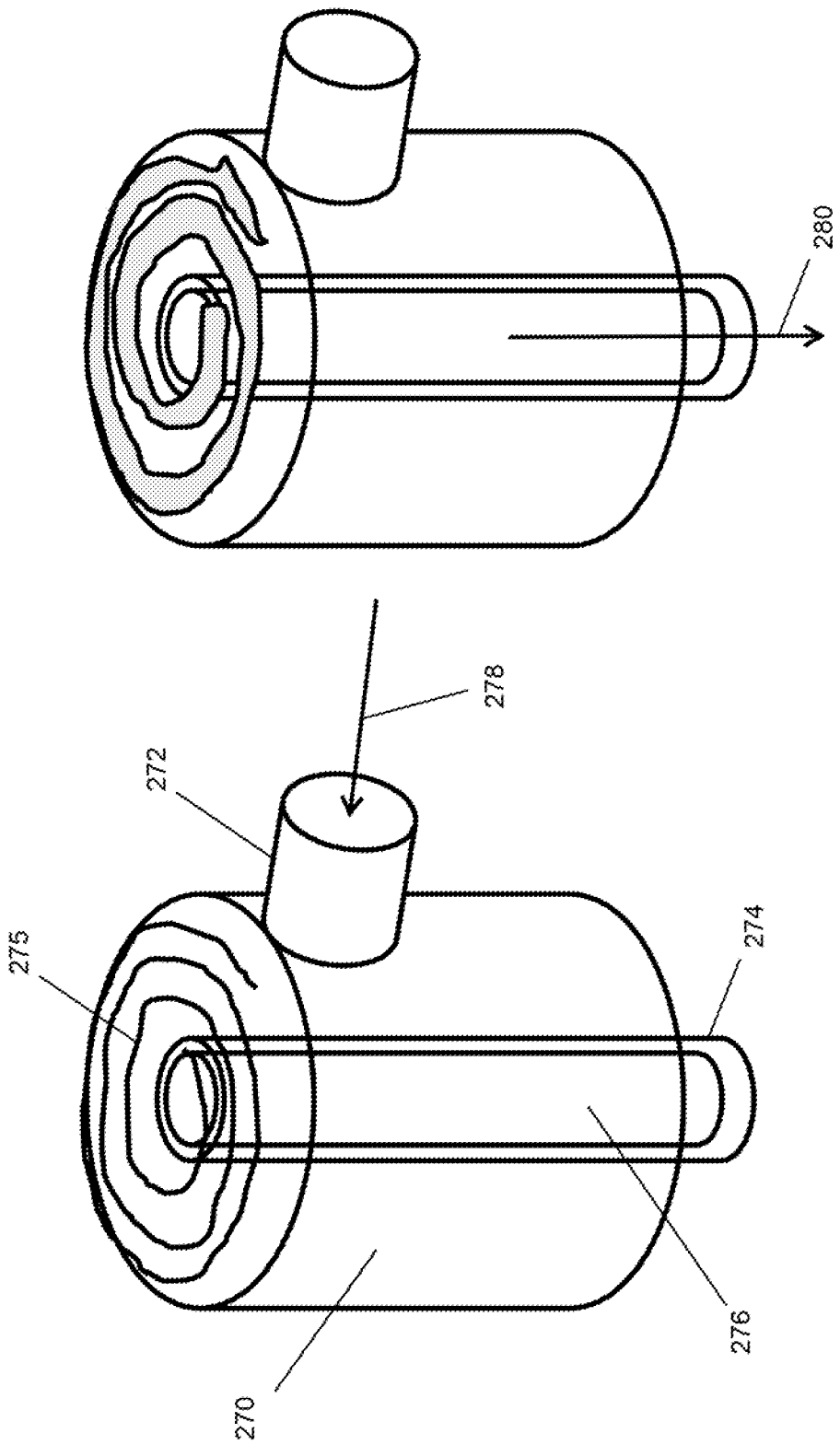

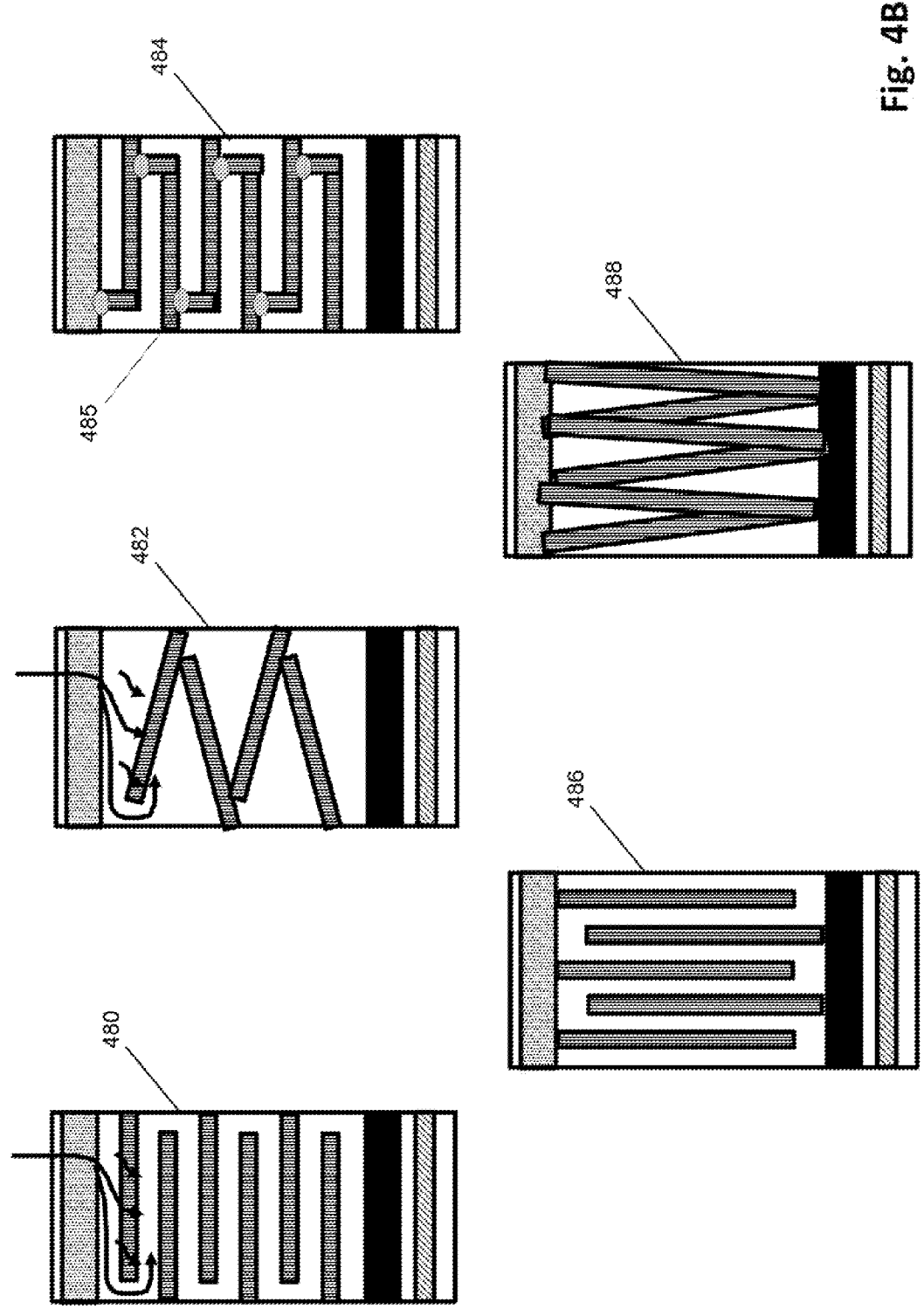

MICROSCALE PLASMA SEPARATOR

This is an application filed under 35 USC 1.371(f) based on International Application serial number PCT/US2015/058731 filed 3 Nov. 2015, which claims priority from U.S. provisional application Ser. No. 62/074,713 filed 4 Nov. 2014 and Ser. No. 62/200,572 filed 3 Aug. 2015. The foregoing applications are incorporated herein by reference.

Blood contains a massive amount of information about the functioning of all tissues and organs in the body. Consequently, blood sampling and analysis are of prime interest for both medical and science applications, and hold a central role in the diagnosis of many physiologic and pathologic conditions. Blood has two main components, plasma and cells, and for a wide range of assays and diagnostic tests, the efficient separation of plasma from cells is highly important.

Many clinical tests and research assays often require the removal of blood cells from plasma, in order to minimize inaccurate results due to particle interference, cell lysis and elevated background signal. Significant advances have been made in the development of portable, compact, and low cost detection technologies, bringing immunoassay and nucleic acid based testing from centralized laboratories to point of care settings. However, sample preparation steps such as, rapid separation of plasma from whole blood is still a challenge that the platform developers have to face. Current standard requires use of laboratory centrifugation instrument, which is bulky and entails specially trained personnel. Current invention provides a disposable unit that can separate plasma from whole blood in 1-2 minutes and is compatible to laboratory and point of care testing platforms.

Successful treatment of HIV/AIDS with high-quality antiretroviral therapy (ART) requires regular viral load (VL) testing at point-of-care (POC) locations. For accurate measurements, plasma must be fractionated from blood, using methods that are typically available only in well-equipped laboratories. The adaptation of quantitative viral testing in resource-limited locations, such as those found at the community level in developing countries, can be accelerated through the development of low-cost blood plasma separation devices that are highly portable, function without electricity, yield enough plasma from a finger stick blood sample, and require no special education or training to operate. The availability of such a device would be critical to widen access to accurate HIV testing at the point of care in resource limited countries, where antiretroviral therapy can greatly reduce HIV-related mortality and morbidity.

There are several unique challenges associated with the development of a standalone blood-plasma separator for VL testing in resource-limited settings. One of them is the sample volume required. The WHO 2013 Guidelines defined virological failure as "persistent viral load readings above 1000 cp/ml". When only 10 µl of plasma is collected from a sample of at least 30-40 µl of blood, amplification and detection accuracy must reach the level of 10 copies (cp) per sample, which pushes the limits of any POC portable testing device, given that highly sensitive laboratory-based instrument such as Roche Cobas TagMan HIV test have detection limits of 20 cp per ml of sample. By this calculation, 100 to 200 µl of plasma would allow for more accurate HIV viral load testing. Current systems confirm this estimate; the Liat™ Analyzer uses a plasma sample volume of about 200 µl. Since healthy adult blood has a plasma range of 35 to 55%, the blood plasma separator must have a capacity for more than 200 µl of blood to extract 100 µl of plasma. Such volumes are large on the microfluidic scale and pose a significant challenge to many microfluidic-based systems.

The second challenge is the processing time. For real-time diagnosis, it is highly desirable for the separation time to be relatively short—on the scale of 1-2 minutes rather than 10-20 minutes. Platforms with flow rates slower than 20 µl/min are therefore precluded, eliminating many choices using micro-fabricated separation structures or tangential flow systems. A third challenge is to carry out plasma separation without lysing cells in the sample which could release contaminating molecules that would complicate or interfere with desired measurements. In manually operated devices fluid movement is typically accomplish by capillary action which lengthens performance time or by plunger driven pressure changes, as with syringes, which may generate very different pressures and pressure changes depending on the user. A fourth challenge is loss of sample through dead volumes in chambers, filters and passages of POC devices. Finally, the requirements for portability, safety and ease of use by personnel without extensive training, and the need to function without electricity impose additional restrictions to any platform under consideration for POC use in resource-limited clinical settings.

Microscale blood-plasma separation has been a very active research area in recent years. Several examples of commercial diagnostic tests integrated with sample preparation platforms have been reported, and advances arising from research and development of microfluidics-based blood-plasma separation systems have recently been reviewed, e.g. Hou et al, Micromachines, (2011) 2: 319-343; Yang et al., Lab on a Chip, (2012) 12(2): 274-280; Toner et al, Annu Rev Biomed Eng, (2005) 7: 77-103. These systems possess a number of advantages, including separation of microliter volumes, miniaturization of the consumable device, integration with downstream sample detection capabilities, and the potential to separate leukocytes and platelets from erythrocytes. However, many of these technologies still require electric pumps for flow control and additional blood dilution steps, or they are constrained by small blood volume throughput, long separation time, and lack of efficiency.

SUMMARY OF THE INVENTION

The invention is directed to methods and devices for rapid fractionation of cells and plasma from small amounts of blood, such as, from 30 µl to 500 µl of blood, obtainable from simple finger-prick blood-drawing techniques, or a blood collection container. In some embodiments, methods and devices of the invention are used for viral load testing, such as for HIV viral load testing in resource-limited settings. In some other embodiments, the devices are used for standard laboratory tests such as electrolyte, lipid, protein and viral RNA analysis that requires the use of plasma.

In some embodiments, the invention is directed to a device for separating plasma from whole blood comprising: (a) a sample collection receptacle with at least one port, the sample collection receptacle capable of holding a predetermined volume of a sample of whole blood drawn through a port; (b) a filter chamber having an inlet and an outlet, and containing at least one filter capable of separating plasma from blood cells as sample passes from an inlet side to an outlet side of the at least one filter whenever the filter chamber is placed in fluid communication with a port of the sample collection receptacle; and (c) a manually driven pump operationally associated with the sample collection receptacle and filter chamber for (i) drawing a predetermined volume of sample into the sample collection receptacle by a first user action and (ii) driving the predetermined volume at a substantially constant linear flow under a pressure not exceeding 2 psi from the sample collection receptacle through the filter chamber and the outlet of the filter chamber by a second user action. In various particular embodiments, the sample collection receptacle may comprise a body and a plunger moveably disposed within the body and forming fluid seals with walls of the body so that by moving the plunger in a first direction a negative pressure is exerted on said sample collection receptacle and by moving the plunger in a second direction, e.g. opposite to that of the first direction, a positive pressure is exerted on said sample collection receptacle. In connection with such latter embodiments, the manually driven pump may include a screw-drive mechanism or a spring-drive mechanism by which the plunger of the sample collection receptacle may be moved.

In some embodiments, the sample collection receptacle may include an elastomeric bladder which may be released from a compressed state to draw sample therein and may be re-compressed, e.g. by rolling up, to drive sample to the filter chamber.

In some embodiments, a device of the invention may comprise: (a) a sample collection receptacle having a first end comprising an inlet, a second end, a first cylindrical wall sealably attached to the first and second ends, and a second cylindrical wall concentric with and enclosing the first cylindrical wall, the second cylindrical wall sealably attached to the first and second ends, the first cylindrical wall comprising a flexible filter material capable of separating plasma from cells in the sample and forming a first interior, the second cylindrical wall comprising a flexible impermeable material and forming a second interior, the first interior and the second interior being in fluid communication solely through the flexible filter material of the first cylindrical wall, the first end and the second end being rotatable with respect to each other, and the first interior being capable of holding a predetermined volume of a sample of whole blood accepted through the inlet; (b) a one-way valve disposed between the inlet and the first interior of the sample collection receptacle to prevent release of sample from the first interior through the inlet; (c) an outlet in fluid communication with the second interior of the sample collection receptacle; and (d) a gripping attachment rigidly attached to either the first end or the second end that permits a user to manually rotate the first end with respect to the second end to twist the first cylindrical wall to contract the predetermined volume of the first interior so that plasma of the sample in the first interior is driven through the filter material into the second interior and is discharged through the outlet.

In still other embodiments, the invention is directed to a device for separating plasma from whole blood with minimal dead volume losses comprising: (a) a sample collection receptacle with at least one port, the sample collection receptacle capable of holding a predetermined volume of a sample drawn through a port, and the sample collection receptacle comprising a chamber with a plunger moveably disposed therein so that sample is drawn into the sample collection receptacle by movement of the plunger in a first direction and sample is forced out of the sample collection receptacle through a port by movement of the plunger in a second direction, the plunger comprising a predetermined volume of inert fluid in a reservoir separated from the sample collection receptacle by a fluid barrier that is capable of releasing the inert fluid into the sample collection receptacle whenever the reservoir is subjected to a predetermined pressure; and (b) a filter chamber having an inlet and an outlet, and containing at least one filter capable of separating plasma from blood cells as sample passes from an inlet side to an outlet side of the at least one filter whenever the filter chamber is placed in fluid communication with a port of the sample collection receptacle.

In some embodiments devices of the invention employ a multi-stage filtration approach that overcomes the limitations of currently available systems including clogging, hemolysis, and slow filtration time. In contrast to current membrane-based systems that use a single filtration material and pore size, in some embodiments, the invention integrates a set of optimized filter materials with a range of pore sizes to construct a multi-stage filtration maze and use chemically induced cell aggregation to allow efficienct removal of all blood cells in 1-2 minutes, without power or additional instrumentation. In some embodiments, devices of the invention can deliver plasma droplets to any POC platform, for example, for HIV viral load testing in resource-limited settings, greatly simplifying and accelerating the use of such platforms.

In one aspect, the invention provides methods and stand-alone devices for microscale plasma separation including a compact, simple-to-use, and low-cost disposable device that will separate plasma from finger stick blood samples, without requiring electrical power or specially trained personnel, and which is compatible with the various point-of-care testing devices. One part of the device allows users to quantitatively measure the amount of blood sample that is picked up into the device by direct visualization. Another part of the device contains a mechanism so that only a pressure between 0.5 to 2 PSI is applied to the blood sample across the separation membrane. In another part, the device contains one-way flow control valve so that the pressure applied cannot be release except through the membrane. In another embodiment, the device contains a mechanism to force all blood samples through the membrane leaving zero-dead volume of unprocessed sample. One part of the device contains a dispenser tip with micro channels to allow dispensing of the separated plasma sample in droplet form into another collection tube or a receptacle on a plasma analyzer instrument. In alternative embodiments, the invention provides multi-stage filter maze for plasma separation. In some embodiments, the invention provides multi-stage filtration in combination with chemically induced aggregation to significantly reduce clogging problems and enable separation of 30 to 500 µl of blood in a 1-2 minute time frame to yield 5 to 200 µl of plasma, respectively.

BRIEF DESCRIPTION OF THE DRAWINGS

FIGS. 2A-2C show close ups of cap designs for use with the embodiment of FIG. 1.

FIGS. 4A-4B show assembly pathways and various geometrical configuration of filters for use in a filter system of the embodiment of FIG. 3.

DETAILED DESCRIPTION OF THE INVENTION

Figure 1:
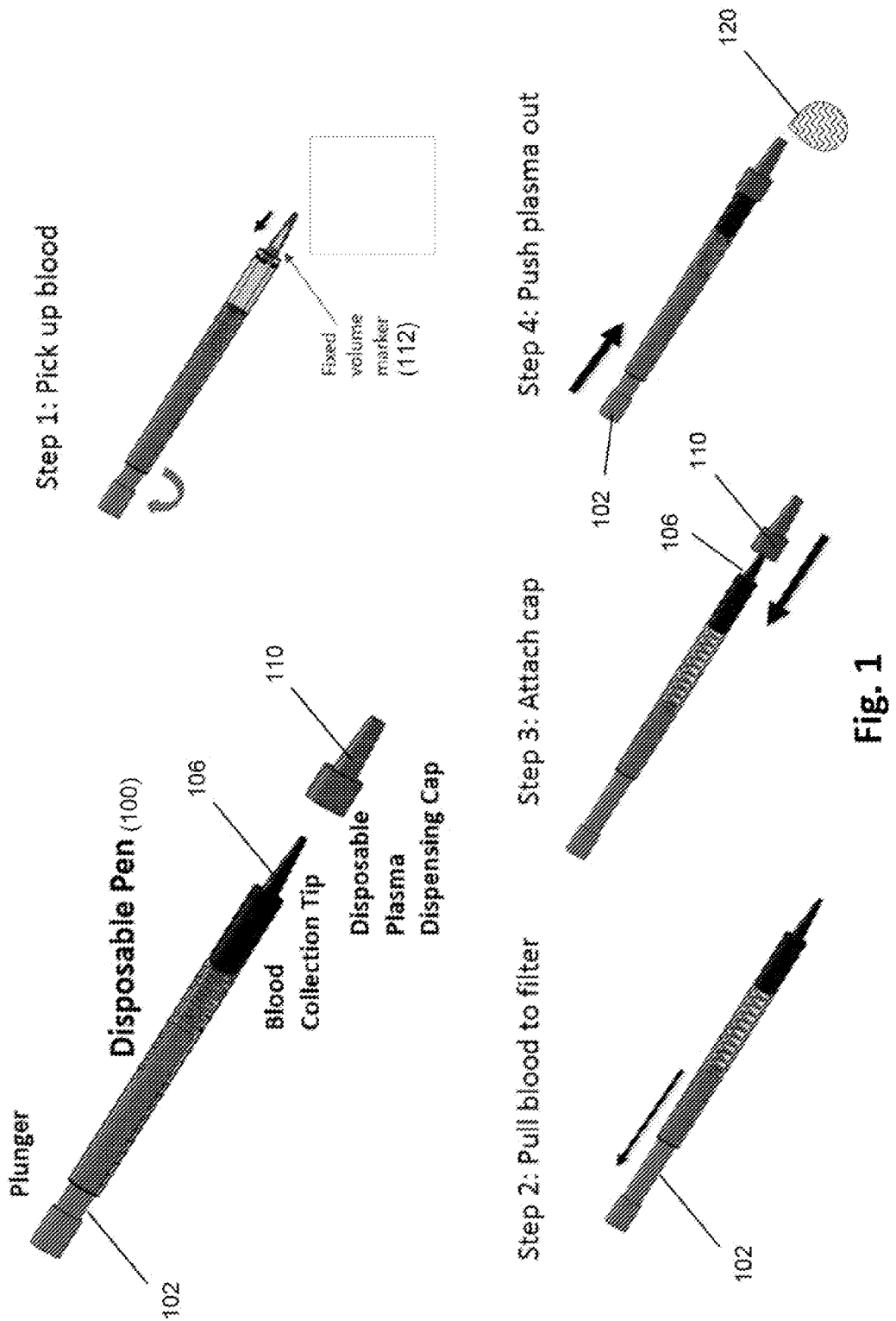
FIG. 1 illustrates the design and operation of an embodiment of the invention employing a spring drive for forcing blood through a filter system with a substantially constant pressure below about 2 psi.

The invention is directed to methods and devices for separating plasma from whole blood which include (i) moving sample and separating sample components by substantially constant low pressures to avoid cell lysing, (ii) manual operation with no electrical or other power source, (iii) minimization of dead volume losses, and (iv) integral design to avoid sample loss or exposure to users. In particular, in some embodiments, devices of the invention comprise a sample collection receptacle into which a sample of whole blood is loaded, a filter chamber containing a filter or a filter system and being capable of being fluidly connected to the sample collection receptacle, and a manually driven pump operationally associated with the sample collection receptacle and/or filter chamber for drawing a predetermined amount of sample into the sample collection receptacle and for directly or indirectly driving the sample in the sample collection receptacle through the filter chamber at a steady pressure less than about 2 psi to effect separation of plasma from the whole blood sample. In some embodiments, the sample collection receptacle includes at least one port or inlet through which sample enters the sample collection receptacle. Such inlet or port may include a one-way valve, or check valve, that prevents sample in the sample collection receptacle from re-entering, exiting through, the inlet or port whenever the pressure in the sample collection receptacle exceeds that in or adjacent to the port or inlet. The sample collection receptacle and/or the inlet or port may optionally include anti-coagulants, e.g. as a coating on an interior surface, or the like, to prevent formation of clots in the sample that could hinder or prevent operation of the device. In some embodiments, the sample collection receptacle is fluidly connected to the filter chamber by a passage that includes a one-way valve, or check valve, which prevents sample from re-entering, or returning to, the sample collection receptacle in case pressure in the sample collection receptacle is lower than the pressure in the filter chamber. In such embodiments, the one-way valves at the inlet to or port of the sample collection receptacle and in the passage to the filter chamber work cooperatively to direct sample from a collection point outside of the device, through an inlet or port into the sample collection receptacle, and to the filter chamber, all with substantially no backflow of sample. In other embodiments, the sample collection receptacle may be connected, e.g. via a lure lock fitting, to a filter chamber after sample has been loaded into the sample collection receptacle. That is, in such embodiments, a device may comprise separate components that are fitted together to complete separation of plasma from blood cells. In such embodiments, one-way valves between a sample collection point (e.g. a blood droplet on a finger from a pin prick) and sample collection receptacle and/or between the sample collection receptacle and the filter chamber are optional. Some embodiments are configured for viral load assays. In some embodiments, a whole blood sample is undiluted. In some embodiments, a predetermined volume, or amount, of sample is in the range of from 30 μL to 500 μL.

A wide variety of manually driven pumps can be used with the invention. In some embodiments, important features of manually driven pumps include (i) operation with no power source besides manual power, and (ii) preclusion of high pressure delivery of fluids or sudden changes in pressure during operation that would cause cells in a blood sample to lyse. Embodiments for carrying out constant low pressure delivery may vary widely and include, but are not limited to, the following specific embodiments: (a) manually compressed or elongated springs that are released to deliver a substantially constant force on a sample collection receptacle (e.g. via a plunger), (b) manually operated screw drives to deliver a constant force on a sample collection receptacle (e.g., again via a plunger), (c) providing a flexible elastic bladder as a sample collection receptacle that may be squeezed to zero, or close-to-zero, volume with a key or screw drive to deliver a constant low pressure on the sample, (d) providing a filter system that encloses a sample, which may be wrung out, thereby reducing its volume to zero, or close-to-zero, thereby forcing at low pressure sample fluid through the filter material, or like manually operated pumps. These and other particular embodiments will be described more fully below.

In some embodiments, an element for minimizing dead volume losses may also be included. In particular, dead volume losses by fluid retention in filters may be minimized by providing a reservoir of fluid that can be driven through the filter chamber, and filters therein, to displace retained plasma so that it exits the device. Fluid delivered by the reservoir can be predetermined so that enough is released to drive substantially all of the plasma from the filter, or filter system, yet not so much as to dilute separated plasma discharged by the device. As described more fully below for a particular embodiment, one element for minimizing dead volume losses comprises a reservoir at one end of a plunger forming a wall of a sample collection receptacle. The reservoir is contained by at least one breakable (or rupturable) wall that can be caused to burst, or rupture, at the end of a plunger stroke so that the reservoirs fluid is release after substantially all sample in the sample collection receptacle has been driven through the filter chamber.

In some embodiments, a device for separating plasma from whole blood with minimal dead volume losses may comprise the following elements: (a) a sample collection receptacle with at least one port, the sample collection receptacle capable of holding a predetermined volume of a sample drawn through a port, and the sample collection receptacle comprising a chamber with a plunger moveably and sealably disposed therein so that sample is drawn into the sample collection receptacle by movement of the plunger in a first direction (e.g. by creation of a negative pressure in the receptacle with respect to the sample volume) and sample is forced out of the sample collection receptacle through a port by movement of the plunger in a second direction (e.g. by creation of a positive pressure in the receptacle with respect to a filter chamber), the plunger comprising a predetermined volume of inert fluid in a reservoir separated from the sample collection receptacle by a fluid barrier that is capable of releasing the inert fluid into the sample collection receptacle whenever the reservoir is subjected to a predetermined pressure; and (b) a filter chamber having an inlet and an outlet, and containing at least one filter capable of separating plasma from blood cells as sample passes from an inlet side to an outlet side of the at least one filter whenever the filter chamber is placed in fluid communication with a port of the sample collection receptacle. In some variations of this embodiment, the fluid barrier comprises a rupturable membrane. Such membrane may be fabricated with a structural weakness that allow such rupturing and/or its rupturing may be facilitated by a sharp protuberance on a wall of the sample collection receptacle opposite the plunger. In some embodiments, the filter chamber has a volume and the predetermined volume of the reservoir is in the range of from 100 percent to 200 percent of the volume of the filter chamber.

The inert fluid may be selected from a wide variety of fluids that are inert in the sense that they do not interfere with analytical reactions on separated plasma. In some embodiments, an inert fluid is selected so that it does not react with any blood component. In some embodiments, an inert fluid may be immiscible with the sample. In other embodiments, an inert fluid may be miscible with sample. Inert fluids may include, but not be limited to, air, water, mineral oil, glycerol, or the like.

In some embodiments, a device for separating plasma from whole blood with minimal dead volume losses may further include elements for low pressure, manually powered movement of fluids. Accordingly, such device may further include a manually driven pump operationally associated with the sample collection receptacle and the filter chamber for (i) drawing the predetermined volume of sample into the sample collection receptacle by a first user action and (ii) driving the predetermined volume at a substantially constant linear flow under a pressure not exceeding 2 psi from the sample collection receptacle through said filter chamber and the outlet of the filter chamber by a second user action.

Cell Aggregation and Crosslinking

In some embodiments, components of a device, such as the sample collection receptacle and/or filter chamber, may include agents to aggregate blood cells in order to prevent obstruction of the filter or filter system by cells. Such aggregation agents, or blood aggregants, include, but are not limited to, cross-linking antibodies, high molecular weight (HMW) polymers, beads, and the like. Exemplary HMW polymers include, hydroxyethyl starch, dextran, polyvinylpyrrolidone, poly-L-glutamic acid, and the like. In some embodiments, HMW polymers include 6% hydroxyethyl starch, 3% dextran (MW>73 kDa), polyvinylpyrrolidone (>360 kDa), poly-L-glutamic acid (>61 kDa), and the like.

In some embodiments, components of a device, such as the sample collection receptacle and/or filter chamber, may include agents to cross-link blood cells in order to prevent obstruction of the filter or filter system by cells. Such cross-linking agents include, but are not limited to, antibodies, or antibody mixtures, specific for predetermined surface antigens on blood cells. Such cross-linking agents may include cross-linking antibodies attached to solid supports, such as, walls or surfaces of device chambers, particles or beads, filters, or filter components, and the like. Exemplary antigens for cross-linking blood cell types include the following: glycophorins for RBCs, CD31 or CD41 for platelets, CD45 for leukocytes, CD34 for stem cells, CD11c for dendritic cells, and the like. Antigens for subsets of leukocytes include the following: CD66b for granulocytes, CD3 for T cells, CD19 for B cells, CD56 for NK cells, and CD14 for monocytes/macrophages.

Use of chemicals to enhance separation efficiency. Various chemicals can be used to induce blood aggregation and enhance separation efficiency, such as various cellulose derivatives, including but not limited to, hydroxyethyl starch, hydroxypropyl cellulose, hydroxyl ethyl cellulose, hydroxybutylmethyl cellulose, dextran of various molecular weight, and polyvinylpyrrilidone. Cross-linking reagents such as melamine, polyepoxide or poly aldehyde can also be added. Chemicals can also include materials such as polyethylene glycol of various molecular weight, branched copolymers, and surfactants to enhance wetting and/or minimize non-specific adsorption of proteins to the filter surfaces. Various concentrations of chemicals can be applied and allowed to dry on the dropper, blood collection channels or one or more filter stages to enhance the plasma separation process. When blood is introduced to the channels and filters, chemical aggregation occurs, allowing filtration of blood cells with large pore size filters.

Figure 7B:
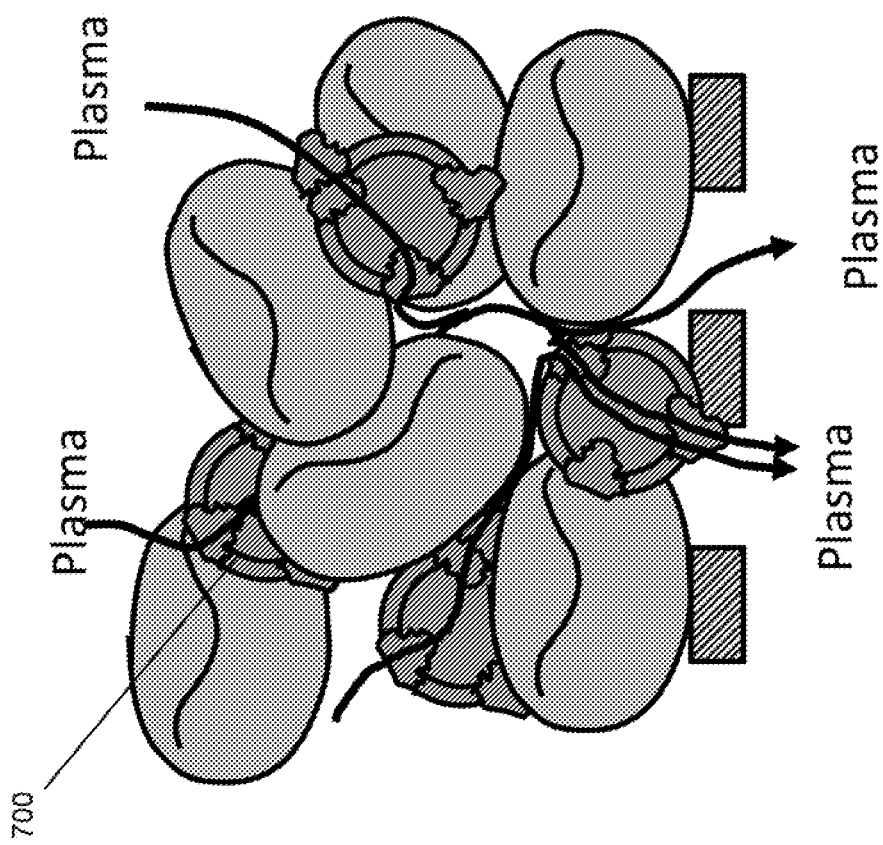
FIGS. 7A-7B illustrate materials from preventing filter clogging due to red blood cell aggregation.
Figure 7A:
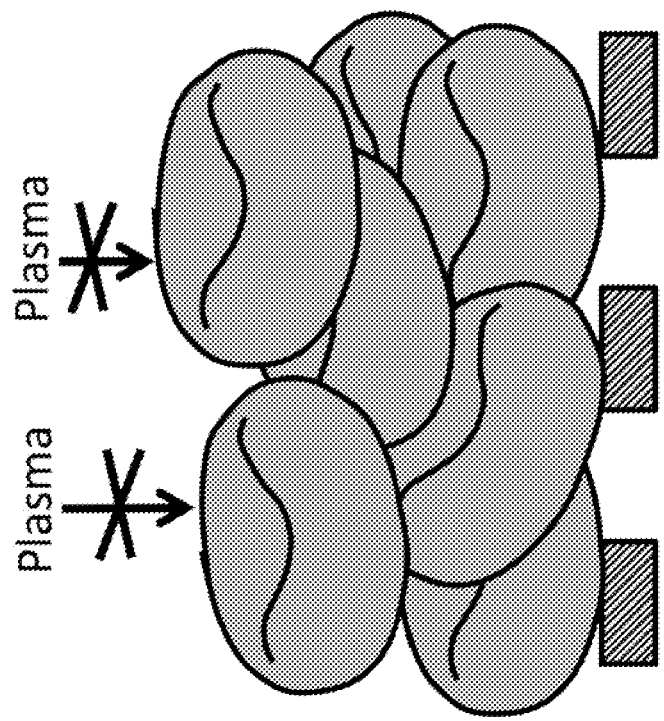

In some embodiments, beads or particles, which may possibly be derivatized as described above, may be combined with a blood sample to create porous aggregations of red blood cells (RBCs). In some embodiments, such particle could work as illustrated in FIGS. 7A and 7B. Without any added agents, RBCs form dense aggregates on the filter surfaces that block plasma flow, as illustrated in 7A, thereby reducing the efficiency of plasma separation. By addition of particles (700), RBCs in aggregates will be spaced apart by the particles to create passages for plasma to flow through, as illustrated in FIG. 7B.

Fluidics, Valves and Fluid Capacities

Elements of devices of the invention may be fabricated using conventional precision molding, 3D printing, and microfluidic device manufacturing techniques. In some embodiments, device elements, such as sample collection receptacle, filter chamber, and the like, have volumes in the range of from a few microliters, e.g. 10 µL, to several hundred microliters, e.g. 500 µL. Selection of particular materials to fabricate such components from is a design choice taking into account requirements of particular applications, including heat and/or cold resistance, chemical inertness, sterility, humidity resistance, ease of manufacturing, cost, and the like.

By spotting or coating chemicals on a portion of a fluidic channel, passive capillary force driven plasma separation can be achieved. Control of flow rate may achieved through control of the fluidic channel's surface wetting properties. In one embodiment, the bottom of the fluidic channel can be coated with chemicals while the top of the channel is composed of hydrophobic plastic, reducing the flow rate of blood inside the channels significantly, allowing dispersion of chemicals, blood cell aggregation, and separation of plasma. In another embodiment, the top and bottom of the fluidic channels are both hydrophobic, and chemicals are spotted onto the bottom or top of the channels.

In some embodiments requiring one-way valves, micromachined one-way valves are disclosed in the microfluidics literature, such as, in Willis et al, NASA Technical Brief NPO-45933; and are available commercially, e.g. miniValve International (Oldenzaal, The Netherlands).

Filters

In some embodiments, whole blood is applied to a multistage filtration unit or filter system. Filter stage 1 (e.g. 40 µm pores) can be a large pore size filter or screen that can contain a chemical coating to induce blood cell aggregation and retention on the filter. Filter stage 2 (e.g. 10-20 µm pores) can be a glass fiber filter that would remove a portion of the blood cells, particularly those not retained by the stage 1 filter. Filter stage 3 can be a single filter with assymetric membrane or multiple filters with final layer pore sizes between 0.5 to 1 µm, or from 1-2 µm, to separate all cells from plasma. The edges of the filters are sealed to ensure that blood will flow only through the filter, not around it.

Filter materials may include glass fiber membranes, cellulose acetate, polyester and polycarbonate track-etched membranes. Filter materials used with the invention may have large variations in structure, and offer different mechanisms for retaining blood cells. In some embodiments, a filter system comprises series of filters comprising different materials, such that fluid of a whole blood sample passes serially through each one. In some embodiments, such a filter system include a first filter which functions to retain blood cells; that is, it functions to prevent blood cells (e.g. RBCs and white blood cells) from passing through the filter, or serves as a barrier to further movement of blood cells through the device.

Exemplary filters include, but are not limited to, GE Lifesciences GF, LF1, MF1, VF2 glass fiber membrane, Porex IB™ model Filter Sampler® Blood Serum Filter, Sterlitech polyester track etch (PETE) membrane, polycarbonate (PCTE) membrane, Essentra blood filtration fiber media, and the asymmetric polysulfone ("ViVid™") membrane of Pall Life Science. In some embodiments, an asymmetric membrane filter is employed. In such filters, the pore size in the material gradually decreases from top to bottom, trapping blood cells effectively. The advantage of this material is its high plasma recovery yield—almost 80% of the theoretically recoverable plasma. The shortcoming of the material is the high surface area required for filtration, with each centimeter square area of the material capable of processing only 20 to 30 µl of blood. When a large volume of blood is applied, the filter becomes clogged. The challenge for integrating this material into the device design is the high surface area required for processing blood volumes of several hundred microliters. In some embodiments, such filters may be used in conjunction with other filter membranes with larger pore sizes in combination with chemical treatment to reduce the amount of red blood cells an asymmetric membrane filter stage.

In other embodiments, glass fiber filters may be used for blood filtration. These materials are used broadly for whole blood assays in lateral flow devices. An advantage of this type of material is the capacity for high flow rate through the materials, i.e., 8 s/cm for Whatman MF1 material. However, large variations in pore size and high liquid absorption are shortcomings. This material may be a good choice for removing a fraction of red blood cells in an early stage of plasma separation. But only relatively small surface area of such material should be used because of its large liquid hold volume.

In further embodiments, track-etched membranes may be employed. For example, Sterlitech membrane is made of thin polycarbonate film with holes etched in the plastic sheet. In addition to consistent pore size, this material does not absorb water, making it an appealing choice for the plasma separation application. Its shortcoming is low pore density. Pores would be expected to become clogged by large numbers of blood cells. Thus, this material will be suitable as a last stage small pore filter to remove the small amount of cells remaining in the plasma sample.

In some embodiments, a filter system is employed comprising a series of at least two stages: a blood cell filtration filter as a first stage, such as a glass fiber filter, and an asymmetric membrane filter as a second stage. In other embodiments, a filter system is employed comprising a series of at least three stages: a blood cell filtration filter as a first stage, such as a glass fiber filter; an asymmetric membrane filter as a second stage; and a small pore filter (e.g. in a range of from 1 to 10 µm diameter) as a third stage, such as a track-etched filter.

In some embodiments, sintered polymer bead filters may be employed. Available from companies such as Porex Corp., large pore size filters of 10 µm to several 100 µm can be custom engineered. This material may be an excellent choice for loading chemicals and to serve as an early stage filter.

In some embodiments, various chemical reagents may be added into the filter material to induce aggregation of red blood cells or cross-linking of cells, in order to use larger pore size filters and higher flow rates. Chemicals may be applied to the surfaces of the porous material by adding the liquid solution on the membrane and allowing the membrane to dry either in air or in the oven. Demonstrated in U.S. Pat. No. 5,895,575 by Kraus and U.S. Pat. No. 5,766,552 by Doshi, such methods can be used to selectively remove leukocytes from platelets and allow rapid separation of red blood cells from plasma. Yang et al. (LabChip, 12(2): 274-280 (2012)) also demonstrated separation of plasma on a uPADs paper-based platform using this approach. A number of low cost chemicals and biochemicals with long shelf life that are known to induce RBC aggregation (Z; Bertolini et al., Bone Marrow Transplant. 1996, 18:783; Neu et. Al., Biophys. J. 2008, 95: 3059; Regidor et al., Exp. Hematology, 1999, 2:380; for HetaSep, for example. In some embodiments, chemical treatment of filter materials may include treatment with:

Hydroxyethyl Starch
Dextran (MW 73 kDa)
PVP (polyvinylpyrrolidone)
P-L-Glu (poly-1-glutamic acid)

Several potential risks are associated with use of these chemicals: they may require time for reaction (which could impact the overall separation time of the device), exhibit inadequate release, or undergo non-uniform mixing into the liquid sample as blood passes through the membrane containing the chemicals. Time-release properties can be optimized by adding wetting agents and adjusting the concentration of chemicals loaded into the filter materials. Mixing of the chemicals with blood can be optimized through choice of filter materials. In addition, one can also incorporate particles such as porous beads that are coated with the chemicals either on top of the filter or inside the filter. One potential advantage of this approach is that the beads may reduce stacking of red blood cells on the filter pores, as shown in FIGS. 7A-7B, allowing plasma to flow through.

In some embodiments, statistical sample bias due to retention of analyte on the filter membrane or plastic fluidic channels, can significantly impact the accuracy of testing results. This risk can be addressed through modification of the chemical formula and filter surface properties to reduce non-specific adsorption. Also of concern, the chemicals added into the filter maze can also potentially impact the down-stream assay testing.

In one aspect, the invention provides multi-stage filtration in combination with chemically induced aggregation to significantly reduce clogging problems and enable separation of 30 to 500 µl of blood and plasma in a 1-2 minute time frame to yield 5 to 200 µl of plasma, and without introducing siginificant analyte bias. Multistage filtration approaches have been used in laminated lateral flow devices for many years, examples of which can be found in U.S. Pat. Nos. 4,987,085 and 4,477,575. Many reports of single membrane-microfluidic hybrid systems also exist in literature, though none can meet all the performance specifications listed here.

Example 1

Cylindrical Plunger-Actuated Microscale Plasma Separation (MPS) Device

An exemplary "pen" design of a device of the invention is illustrated in FIG. 1. The pen may include a disposable tip for drawing up blood from the fingertip surface or secondary blood sample container. A spring-loaded plunger draws blood through a filter stack that is integrated inside the tip. A second disposable cap at the end of the tip encloses the blood contaminated tip and seals the entrance end of the tip. The cap contains built-in microfluidic channels. When the plunger is pushed, plasma collected at the end of filter maze is pushed through the channels in the cap and forced out through the tip of the cap, while captured cells remain on the filter surfaces. Some embodiments are configured for viral load assays.

In one aspect, the invention includes a microscale plasma separation (MPS) device that meets the following performance criteria:
 a) The device processes 30 to 500 ul of blood and expel 10 to 200 ul of plasma, respectively;
 b) The separation time is no longer than 2 minutes, preferably under one minute;
 c) The device does not introduce significant sample bias;
 d) It is low cost and disposable, preferably with total cost of less than $1;
 e) The device is compact, no larger than a ball point pen, and require no electricity to operate;
 f) It is simple and intuitive to use require only standard safety precautions for use.

In some embodiments, the MPS device is a microfluidic system with integrated filter membranes. To achieve rapid separation of blood in 1-2 minutes, a multi-stage filtration system is used which is constructed with a set of filters of various pore sizes and chemical compositions that will fractionate blood cells incrementally. Filter pore size decreases from large to small, removing a fraction of the cells at each stage. An advantage of the multi-stage filter maze approach is that larger pore size filters can be used at the earlier stage to allow higher flow rate, and the gradual reduction in cell numbers mitigates the problem of clogging at the later stage in small pore size filters. In addition, chemicals adsorbed and dried inside the filters are released during flow to induce aggregation. The aggregated RBC are less deformable, and can be filtered out with larger pore size filters, further reducing probability of clogging at smaller pore size filters.

In one aspect, the invention includes methods and apparatus for evaluating multistage filter assemblies. Such methods and apparatus permit a variety of filter configurations and chemical treatment combinations to be evaluated experimentally as described below. This device enables iterative combinatorial testing of filter materials, device matrices, and chemical pretreatments to accelerate optimization and confirm the feasibiliy of multi-stage filteration for rapid plasma sepration. An example of multistage approach is as follows:
 Filter stage 1: 40 µm cell strainer, as used often in flow cytometry to remove impurities and large aggregates in the sample.
 Filter stage 2: 10-20 µm filter to retain induced-aggregated blood cells by using chemically coated filters.
 Filter stage 3: 1-2 µm filter to remove the remaining blood cells.
 Filter stage 4: Combination of plasma wicking membrane to collect the plasma and microfluidic channels with hydrophilic surface treatment to funnel the plasma to the collection point via capillary force.

In some embodiments, a filter maze will be integrated into a disposable tip unit that is part of the complete MPS Pen, affording rapid separation of plasma in a device that resembles a ball point pen in size and operation. The MPS pen design provides a compact stand alone device, which the user can use to draw blood from the patient finger tip or a blood collection tube, and expel plasma by simply attaching a cap to the blood pick up tip.

In one aspect of the invention, a multi-stage filtration system is integrated into a simple-to-use product, the MPS Pen. A schematic drawing of operation of the device is shown in FIG. 1. The MPS Pen shown has two components: the disposable pen (100) with a tip (106) for drawing blood, and a disposable cap (110) for enclosing the blood collection tip with outlet bores for dispensing plasma. In step 1, the tip is used to draw blood from a sample collection device or finger tip; the transparent plastic tip has a marked line to alert user that a fix volume (112) of sample (for example, 300 ul) has been collected. In step 2, the plunger (102) is moved upward through a spring loaded mechanical component with a simple catch, pulling blood into the multi-stage filter integrated inside the collection tip. In step 3, a disposable cap (110) is attached to the tip (106), sealing the end of blood pick-up inlet hole and preventing contamination from the tip. In step 4, the plunger (102) is pushed downward to push out plasma (120) from microbores at the end of the cap.

Figures 2A, 2B:
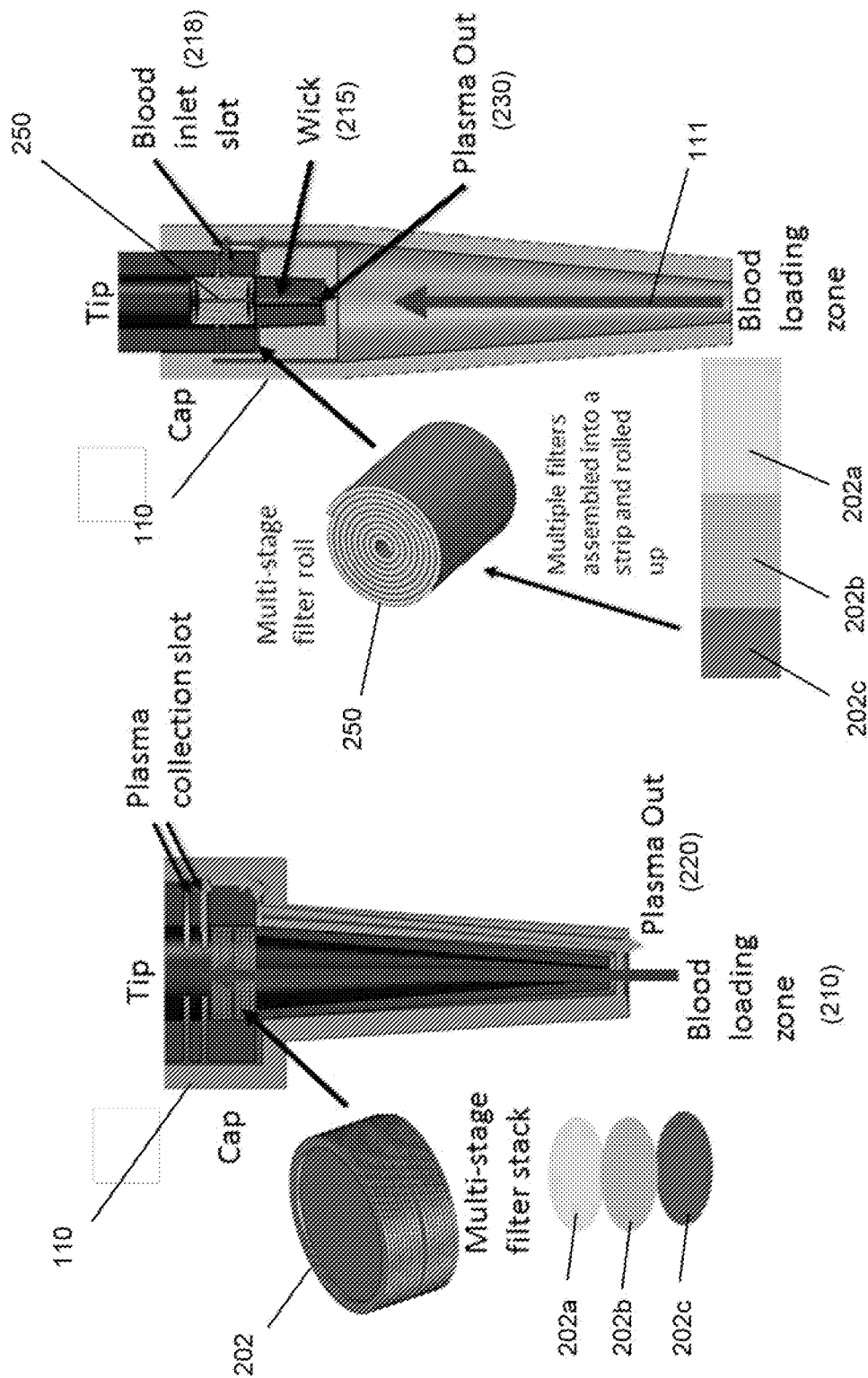

In some embodiments, such results are achieved using a relativly small diameter (8-15 mm) filters, inserted inside tip (106). As shown in FIG. 2A (202), various layers of filter (of different pore size and chemical composition, for example for stage 1, stage 2 and stage 3 filters, shown as 202a, 202b and 202c, respectively) can be laminated on top of each other with the edge sealed by laser cut pressure sensitive adhesive rings, or by applying physical pressure using o-rings to seal the edge of the filter to prevent leakage around each of the filters. However, it is also likely that larger filter surface area will be required to process blood volumes approaching 500 µL. This can be achieved by using a roll design (250 in FIG. 2B), similar to that used in electrolytic capacitor, where layers of dissimilar materials are rolled together to create large surface area in compact space.

Integration of the second disposable component, the cap, will prevent contamination and allow a separate outlet for the plasma. In one possible design (FIG. 2A), blood is pulled into the filter stack from the bottom by the negative pressure generated by the plunger movement (FIG. 1, step 2). One then attaches a cap to the blood collection tip (FIG. 1, step 3). The cap is designed to snap onto the blood collection tip (210) through a one way plastic snap, so that the cap cannot be removed reversibly; this design is meant to minimize blood contamination. The cap contains an inner sleeve that seals in the blood collection tip to minimize possible contamination from blood on the outside of the tip and to prevent air from leaking out the end of the tip. The user then pushes on the plunger (FIG. 1, step 4) and plasma collected at the end of the filter matrix is pushed out through the plasma collection slot and dispensed through the plasma dispensing hole (220) (FIG. 2A).

In a alternative design when a filter roll is used, functions of the cap and tip are reversed. In this design, illustrated in FIG. 2B, cap (110) is pre-attached to the tip, and blood is first drawn into the loading zone (111) of cap (110). Negative pressure is applied to the center of the filter roll through a rod or wick (215) inserted to the middle of the filter roll using the same upward plunger action, and blood is pulled through the filter roll from outside (218) toward the middle. The center rod is fabricated from a soft porous wicking material similar to those used inside felt tipped pens, which will absorb plasma separated by the filter roll. The user then removes the cap, exposing the clean tip. By pushing on the plunger, the center rod is detached from the filter roll and forced into the dispensing tip (230). The tip is shaped such that its diameter gradually decreases, exerting force onto the wicker rod squeezing out the plasma (FIG. 2B). An embodiment of a filter chamber adapted for a filter roll is illustrated in FIG. 2C. Filter chamber (270) with inlet (272) and outlet (274) contains filter roll (275) and wicking member (276) at the center of filter roll (275). During operation, a sample of whole blood enters (278) inlet (272) and is driven to filter roll (275) where plasma is separated from blood cells and collects in wicking member (276) after which it is discharged through outlet (280).

The tip and cap components may be fabricated using standard machining or 3D printing technologies. The filter stack may be fabricated using pressure sensitive adhesives. The filter roll may be fabricated using a special type of porous pressure sensitive adhesive web that provide adhesion to the multiple materials. Attention should be paid to proper sealing around the filter to prevent leakage, as this is very important for the functionality of the device. A filter housing insert with gaskets may be added to ensure proper sealing around the perimeter of filter stack or the top and bottom edges of filter roll.

In some embodiments, the front of the tip of the MPS pen has a loading zone (210 in FIG. 2A and 111 in FIG. 2B) for blood samples. The volume may be predefined by the shape of the tip depending on the amount of blood and plasma requirements by the user. For example, just like pipet tips, one can have a tip that has a loading capacity of 200 µl, but can only produce 60 µl of plasma, or another tip that has a loading capacity of 500 µl, and can produce 150 µl of plasma. The device can carry different tip options to suit application needs. The tip may be made with transparent plastic so the user can fill blood to the top of the loading zone where it is clearly marked. The user may have to collect blood from several lanced fingers since it is very difficult to collect 500 µl of blood from a single finger prick. A gradual filling of the tip will allow maximum user control, which ensures complete filling of the loading zone and avoids pulling air into the tip. The design may use a thread mechanism in which, by turning the plunger, the plunger is moved upward gradually, allowing the user to pull in the amount in a controlled fashion (similar to the embodiment of FIG. 6A). Both the tip and the cap can also be hydrophilic and may contain chemicals and/or microchannels that support liquid movement via capillary force.

Example 2

Spring-Driven Plasma Separator With Multiple Filter Systems

Figure 3:
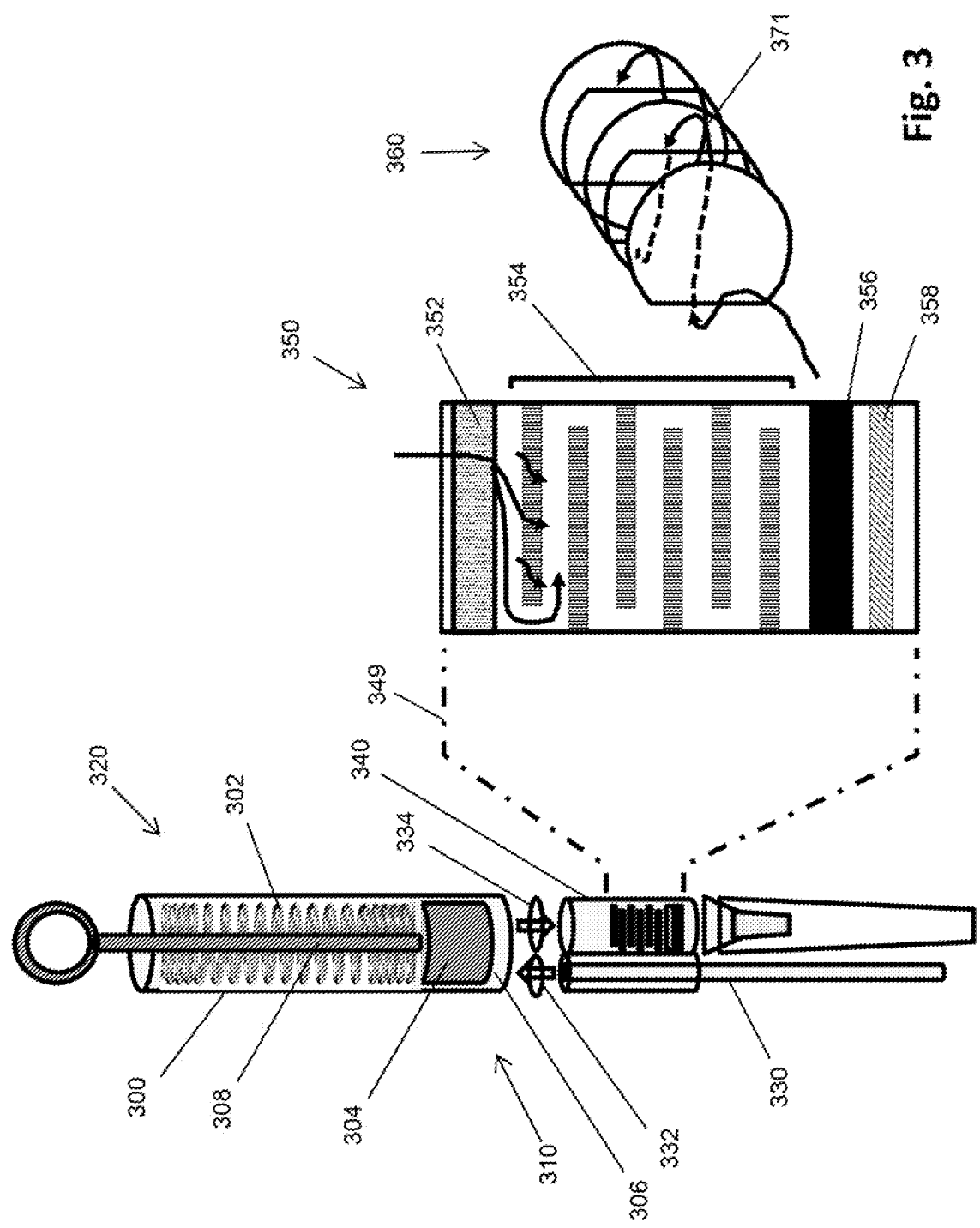
FIG. 3 illustrates another spring-drive design with a blow-up of a filter system.

Components of another embodiment of a microfluidic plasma separator are illustrated in FIG. 3. Cylindrical body (300), having first end (310) and second end (320), contains compression spring (302) and plunger (304) which is moveable along the axis of cylindrical body (300) and which forms a seal with the inner wall of cylindrical body (300), thereby forming sample collection receptacle (306) at first end (310) of cylindrical body (300). Plunger (304) is configured with lever (308) which permits plunger (304) to be manually moved between first end (310) and second end (320). Lever (308) also permits spring (302) to be compressed. Optionally cylindrical body (300) may include a mechanical catch (not shown) to reversibly hold compression spring (302) in a compressed state until it is manually released, which then allows spring (302) to de-compress and push plunger (304) toward first end (310) of cylindrical body (300) which, in turn, reduces the volume of sample collection receptacle (306) and creates a positive pressure on any fluid contained therein. It would be understood by one of ordinary skill that embodiments with different spring types may be used, including but not limited to, a compression spring that is place in an over stretched state, then released to drive fluid through filters as it moves to a relaxed state.

Inlet tube (330) is fluidly connected to sample collection reservoir (306) by one-way valve (332) which allows sample to enter sample collection reservoir (306) but prevents backflow of sample from sample collection reservoir (306) to inlet tube (330) whenever the pressure in sample collection reservoir (306) exceeds that of the interior, or bore, of inlet tube (330). Through a separate port, sample collection receptacle (306) is fluidly connected to filter chamber (340) by one-way valve (334) which allows sample to enter filter chamber (340) but prevents backflow of sample from filter chamber (340) to sample collection receptacle (306) whenever pressure in filter chamber (340) exceeds that of sample collection reservoir (306). Inlet tube (330), sample collection receptacle (306), one-way valves (332 and 334), spring (302) and plunger (304) cooperate to load sample into sample collection receptacle (306) by movement of plunger (304) toward second end (320) of cylindrical body (300) and to force loaded sample to flow into filter chamber (340) through one-way valve (334) upon release of compressed spring (302) which drives plunger (304) toward first end (310), thereby applying a low substantially constant pressure on sample in sample collection receptacle (306). In some embodiments, compression spring (302) is selected to have a spring rate and geometry (e.g. relaxed length, width, wire thickness, composition, and the like) so that the pressure on the sample does not exceed 2 psi.

Blow-up (349) illustrates an embodiment of a filter system (350) in filter chamber (340) comprising four stages as described above: filter stage 1 (352), filter stage 2 (354), filter stage 3 (356), and filter stage 4 (358). Flow of sample components, e.g. plasma, through filter system (350) is indicated by arrows (353). Flow of sample components is also illustrated in perspective view (360) of filter system (350) by arrows (371).

Figure 4A:
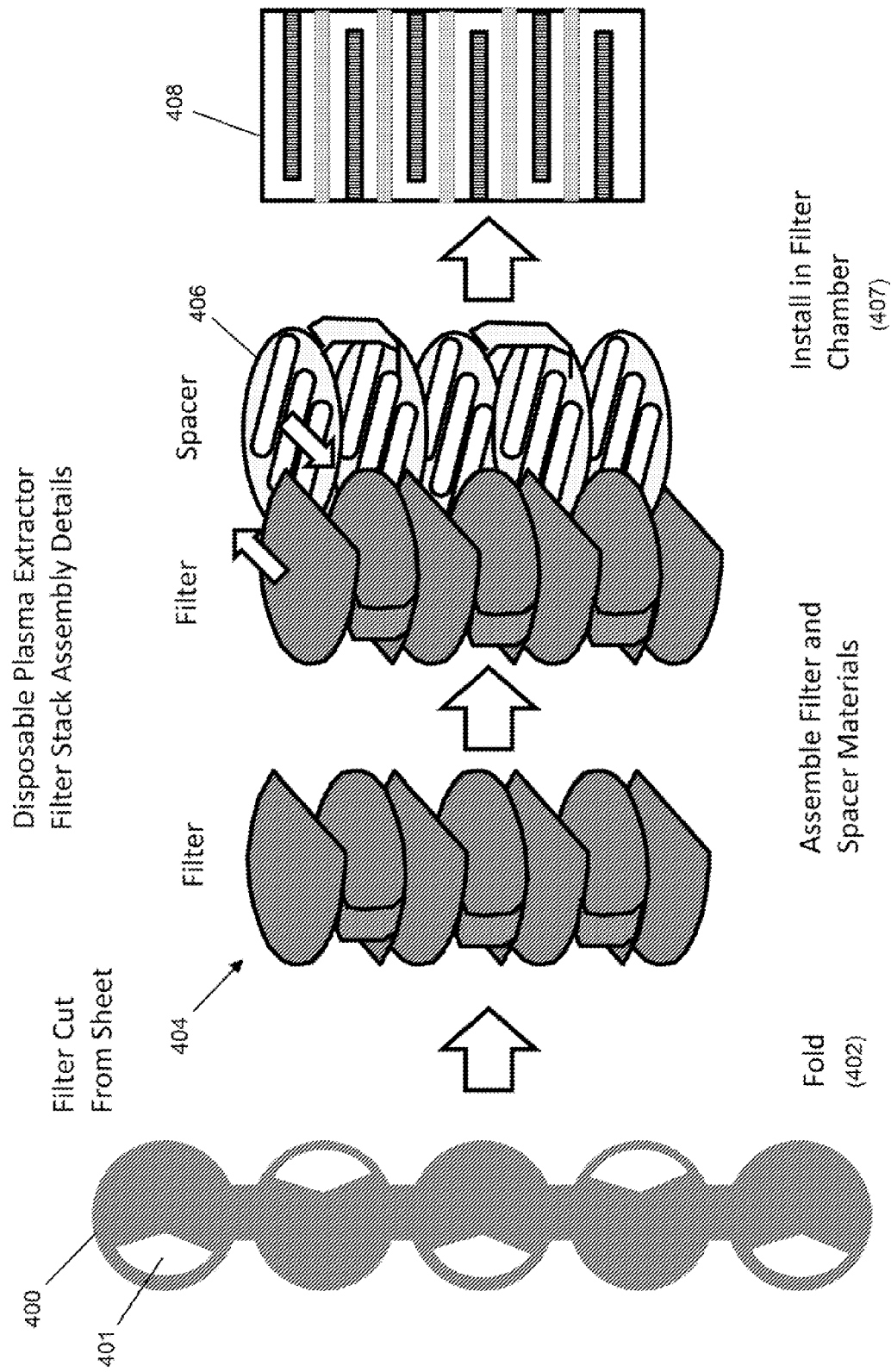

Filter system (350) may be manufactured and assembled as illustrated in FIG. 4A. Filter material (400) may be cut (including holes (401) for fluid passage) from a sheet and folded (402) to form three-dimensional shape (404) suitable for installing in a filter chamber. In some embodiments, spacers (406) may be manufactured similarly and combined with folder filter (404) for installation in filter chamber (408). A wide variety of filter systems (350) are possible by varying the compositions and specifications of component filter elements and their geometries. Several possible geometries of stage 2 filters are illustrated in FIG. 4B. These include, but are not limited to, planar geometry (480), angled geometry (482), soluble connector geometry (in which filters are assembled with soluble glue (485)), longitudinal geometry (486), angled longitudinal geometry (488), and the like.

Example 3

Screw-Driven Plasma Separator

Figure 5A:
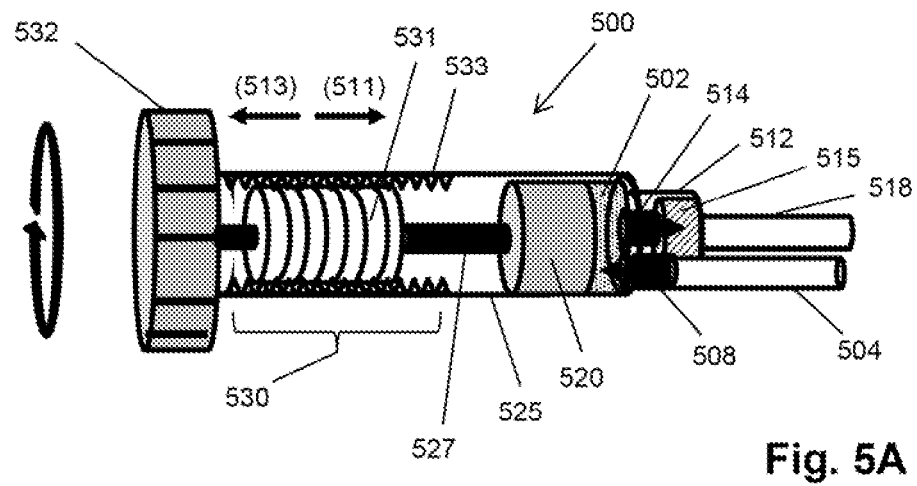
FIG. 5A illustrates a screw-driven movement for driving a plunger manually at low substantially constant pressures.

As mentioned above, another embodiment of a manually driven pump to deliver substantially constant low pressure to sample is illustrated in FIG. 5A. This embodiment is substantially the same as that of FIG. 3, except that a screw-driven manual pump is substituted for a spring-driven pump. Device (500) comprises sample collection receptacle (502) fluidly connected to inlet tube (504) through port (504) and one-way valve (508). Sample collection chamber (502) is also fluidly connected to filter chamber (512) through one-way valve (514). Sample collection receptacle (502), one-way valves (508 and 514), plunger (520), and inlet tube (504) cooperate as described above to draw in a volume of sample and to drive it into and through filter chamber (512). Filter chamber (512) contains filter and/or filter system (515) and has outlet (518) on downstream side of filter (515). Plunger (520) is sealingly fitted into cylindrical body (525) and rigidly connected to shaft (527) which, in turn, is rotatably connected to screw-drive mechanism (530) which, in turn, is rigidly connected to knob (532). In some embodiments, screw-drive mechanism comprises threads (531) that are operationally associated with complementary threads (533) on cylindrical body (525), so that by a first rotation (e.g. counter-clockwise) the plunger exerts a negative pressure on the sample collection receptacle (502) and by a second rotation (e.g. clockwise) the plunger exerts a positive pressure on the sample collection receptacle (502). Screw mechanism (530) is configured so that by manually turning knob (532) a user may move plunger (520) forward (511) or backward (513) axially through cylindrical body (525), thereby decreasing or increasing by small increments, respectively, the volume of sample collection receptacle (502) and/or increasing or decreasing by small increments, respectively, pressure on fluid contained in sample collection receptacle (502). In some embodiments, size of knob (532), threads (531), and mechanical resistance to turning are selected so that manual operation, that is, an ordinary user manually turning knob (532), produces pressures on sample in sample collection receptacle (502) that do not exceed 2 psi.

Example 4

Plasma Separator Employing Elastic Bladder

Figure 5B:
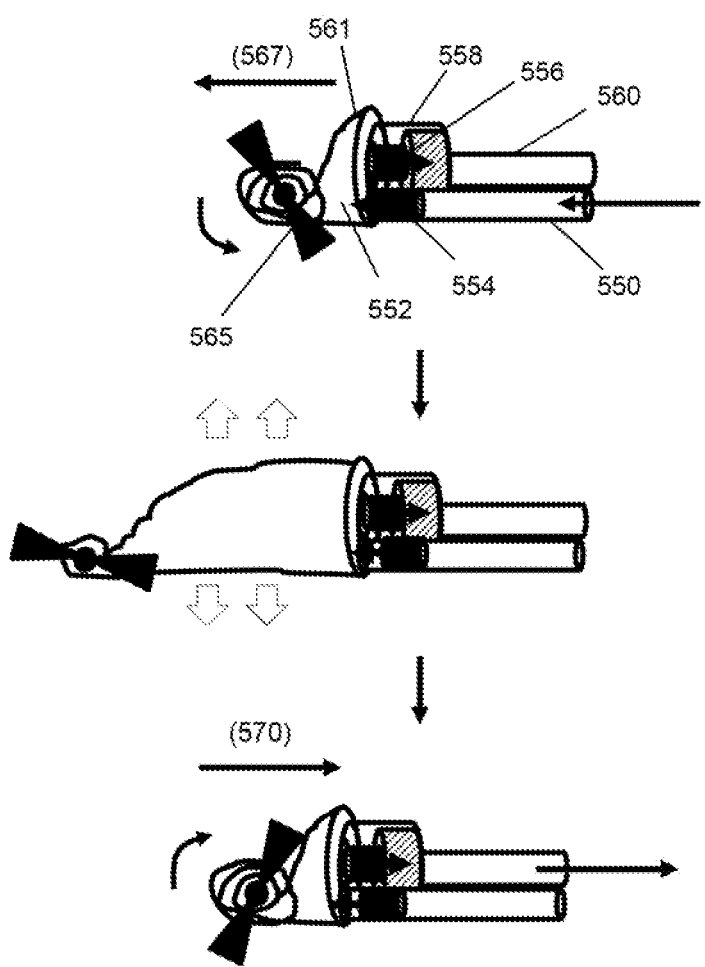
FIG. 5B illustrates an embodiment with fluid delivery using an expandable bladder that may be emptied at low pressure by a manually operated wind-up key.

Another embodiment of a manually driven pump to deliver substantially constant low pressure to sample is illustrated in FIG. 5B. As above, this embodiment is substantially the same as that of FIG. 3, except that the spring-driven pump of FIG. 3 is replaced by a manually driven pump that employs an elastic bladder that is capable of being manually unrolled and rolled to draw in sample and to expel sample from a sample collection receptacle. Inlet tube (550), sample collection receptacle (552), one-way valves (554 and 556), filter chamber (558), and outlet (560) work in substantially the same way as described above. Sample collection receptacle (552) comprises elastic bladder (561) that may be rolled up, for example, using key (565) connected to a shaft (not shown) bonded to one end of elastic bladder (561). Key (565) may be manually turned to roll-up or roll-out elastic bladder (561) to decrease or increase, respectively, the volume of sample collection receptacle (552) by small increments, or to increase or decrease, respectively, the pressure on sample fluid contained in sample collection receptacle (552). That is, by rotating key (565) in a first direction (e.g. counter-clockwise), the volume of elastic bladder (561) is increased thereby creating a negative pressure in sample collection receptacle (552) that allows sample to drawn into such receptacle. By rotating key (565) in a second direction (e.g. clockwise), the volume of elastic bladder (561) is decreased thereby creating a positive pressure in sample collection receptacle (552) that drives sample into filter chamber (558). In some embodiments, elastic bladder (561) may have a tubular shape when in a relaxed state, similar to in shape and composition to an eye dropper bulb. When elastic bladder (561) is deformed from its relaxed state, the material comprising elastic bladder (561) exerts a force, or forces, on the walls to return them to a relaxed state. Thus, when elastic bladder (561) is unrolled (567), it reverts to its relaxed shape and creates negative pressure in sample collection receptacle (552) and allows device to draw in sample as the elastic bladder expands and returns to a relaxed state. Conversely, when elastic bladder (561) is rolled up (570), it creates a positive pressure in sample collection receptacle (552) which drives sample into and through filter chamber (558). Key (565) may be mounted in a frame that includes a mechanism for regulating the rate of rolling either for loading sample collection receptacle (552) or for driving sample therein through filter chamber (558). For example, mechanical resistance may be applied to the shaft connect to key (565) to increase the amount of torque required for turning key (565), or a ratchet mechanism may be employed to increase the amount of manual activity to roll-up elastic bladder (561) a unit amount.

Example 5

Manually Driven Pump By Wringing

Figure 6A:
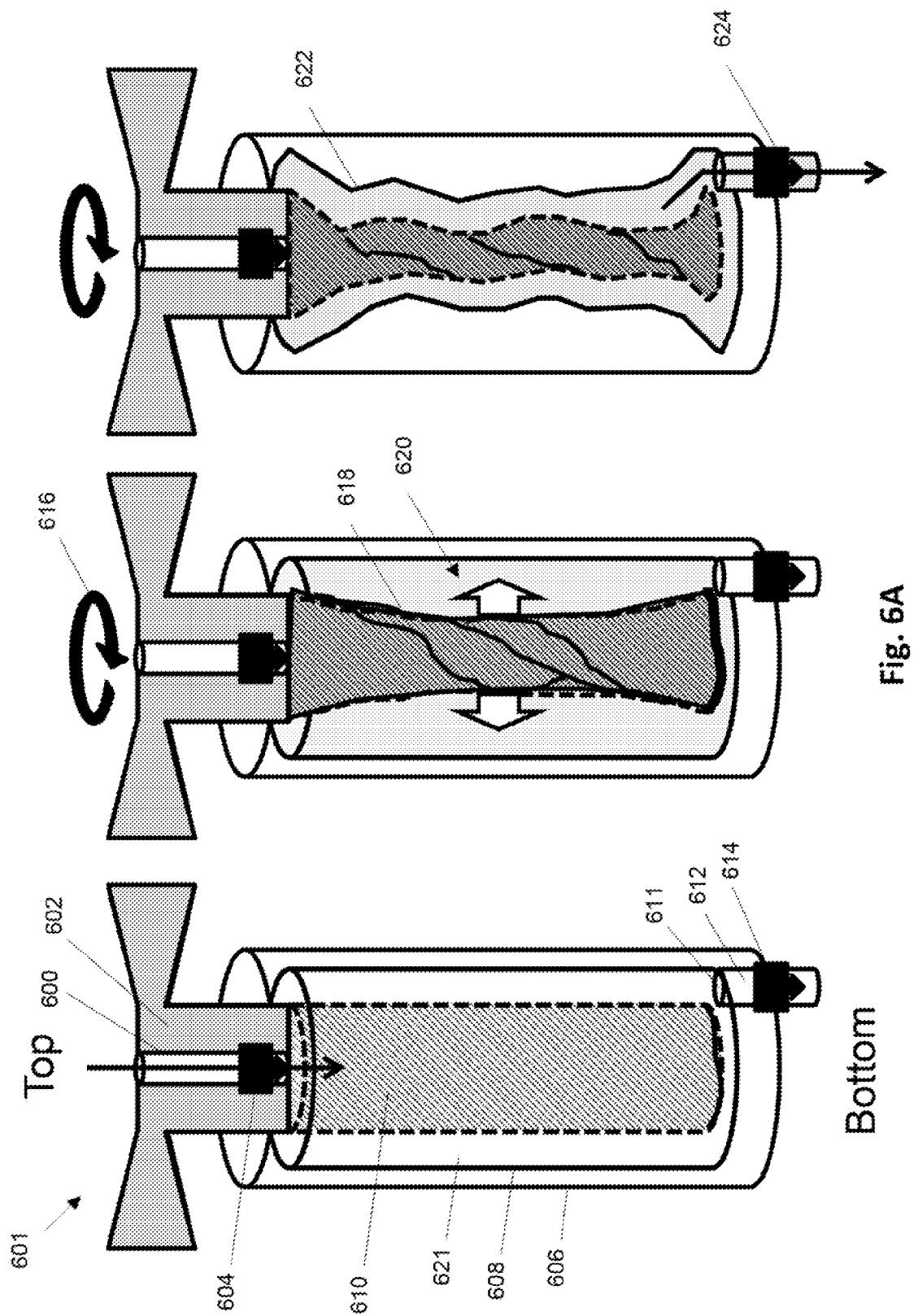
FIGS. 6A-6B illustrate embodiments of the invention employing mechanisms for wringing plasma out of a filter material.
Figure 6B:
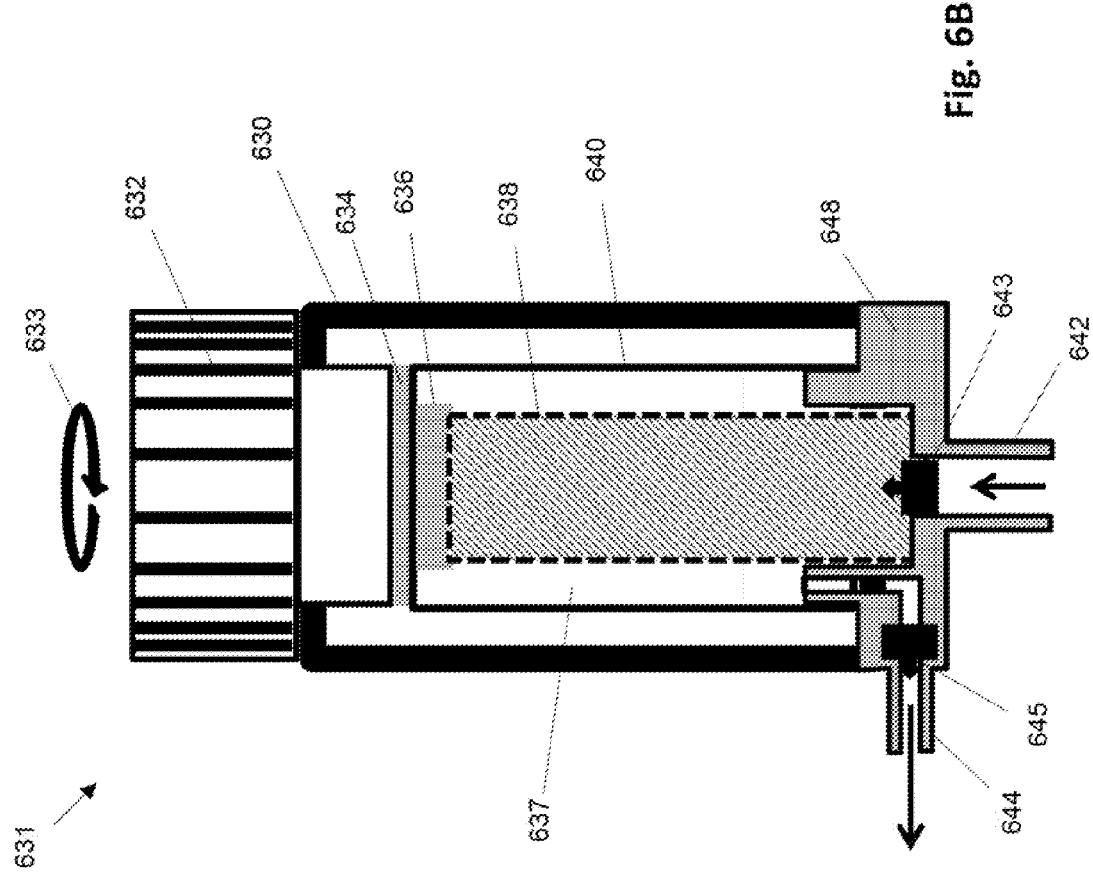

FIGS. 6A-6B illustrate different embodiments of devices with manually driven pumps that move sample through a filter system by wringing the filters. The illustrated devices differ in their arrangements of inlet and outlet with respect to the position of a wringing mechanism for collapsing the filters. Otherwise, the principle of operation is the same for the embodiments. If the position of the wringing mechanism is taken as the "top" of the device and the opposite end of the device is taken as the "bottom" of the device, then the inlet-out arrangements of the illustrated embodiments is as follows: FIG. 6A: top-bottom; FIG. 6B: bottom-bottom. Other arrangements of inlets and outlets are within the scope of the invention.

In FIG. 6A, device (601) comprises body (606) with outlet (612) containing one-way valve (614) at the bottom of the device and mounted therein mechanism (602) at the top of the device sealingly and fixedly attached (e.g. by adhesive) to filter container (610) and impermeable container (608). Inlet (600) extends axially through mechanism (602) and contains one-way valve (604). Filter container (610) and impermeable container (608) are fixedly attached (e.g. by adhesive) to the bottom of body (606) such that port (611) to outlet (612) is exterior to impermeable container (608). Mechanism (602) is rotatable with respect to the bottom of body (606) such that whenever mechanism (606) is turned with respect to body (606) a twisting, or wringing, motion is applied to filter container (610) and impermeable container (608), which are fixedly attached to the bottom of body (606). In operation, sample is loaded into filter container (610) through inlet (600) and one-way valve (604), which prevents return of sample into inlet (600). As mechanism (602) is turned (616), filter container (610) is collapsed (618) which reduces its volume, thereby forcing sample through the wall (620) of filter container (610) and into cavity (621) between the outside surface of filter container (610) and the inner surface of impermeable container (608). Impermeable container (608) comprises a pliable but impermeable material, so that as mechanism (602) continues to be turned, impermeable container is cause to collapse (622) thereby reducing the volume of cavity (621) and placing pressure on the filtrate, that is, the plasma, from filter container (610). Such pressure then drives the separated plasma through outlet (624).

In FIG. 6B, device (631) comprises body (630) with outlet (644) and one-way valve (645) and inlet (642) and one-way valve (643) mounted in base member (648) at the bottom of device (631). Body (630) encloses impermeable container (640) which, in turn, encloses filter container (638) producing cavity (637). Both impermeable container (640) and filter container (638) are fixedly and sealingly attached (e.g. with adhesives) to base member (648) and to mechanism (632) at the top of device (631). Mechanism (632) is rotatable with respect to base member (648), so that when it is turned (633) filter container (638) and impermeable container (640) are cause to collapse and to drive sample components, such as plasma, from the interior of filter container (638) into cavity (637) and further through outlet (644) as impermeable container (640) collapses.

In some embodiments, the above devices for separating plasma from whole blood comprise the following elements: (a) a sample collection receptacle having a first end comprising an inlet, a second end, a first cylindrical wall sealably attached to the first and second ends, and a second cylindrical wall concentric with and outside of the first cylindrical wall sealably attached to the first and second ends, the first cylindrical wall comprising a compliant filter material capable of separating plasma from cells in the sample and forming a first interior, the second cylindrical wall comprising an impermeable material and forming a second interior, the first interior and the second interior being in fluid communication solely through the filter material of the first cylindrical wall, the first end and the second end being rotatable with respect to each other, and the first interior being capable of holding a predetermined volume of a sample of undiluted whole blood accepted through the inlet; (b) a one-way valve disposed between the inlet and the first interior of the sample collection receptacle to prevent release of sample from the first interior through the inlet; (c) an outlet in fluid communication with the second interior of the sample collection receptacle; (d) a mechanism including optionally a gripping attachment, the mechanism rigidly attached to either the first end or the second end that permits a user to manually rotate the first end with respect to the second end to contract the predetermined volume of the first interior so that plasma of the sample in the first interior is driven through the filter material into the second interior and is discharged through the outlet.

Example 6

Reducing Dead Volume Losses

Figure 8:
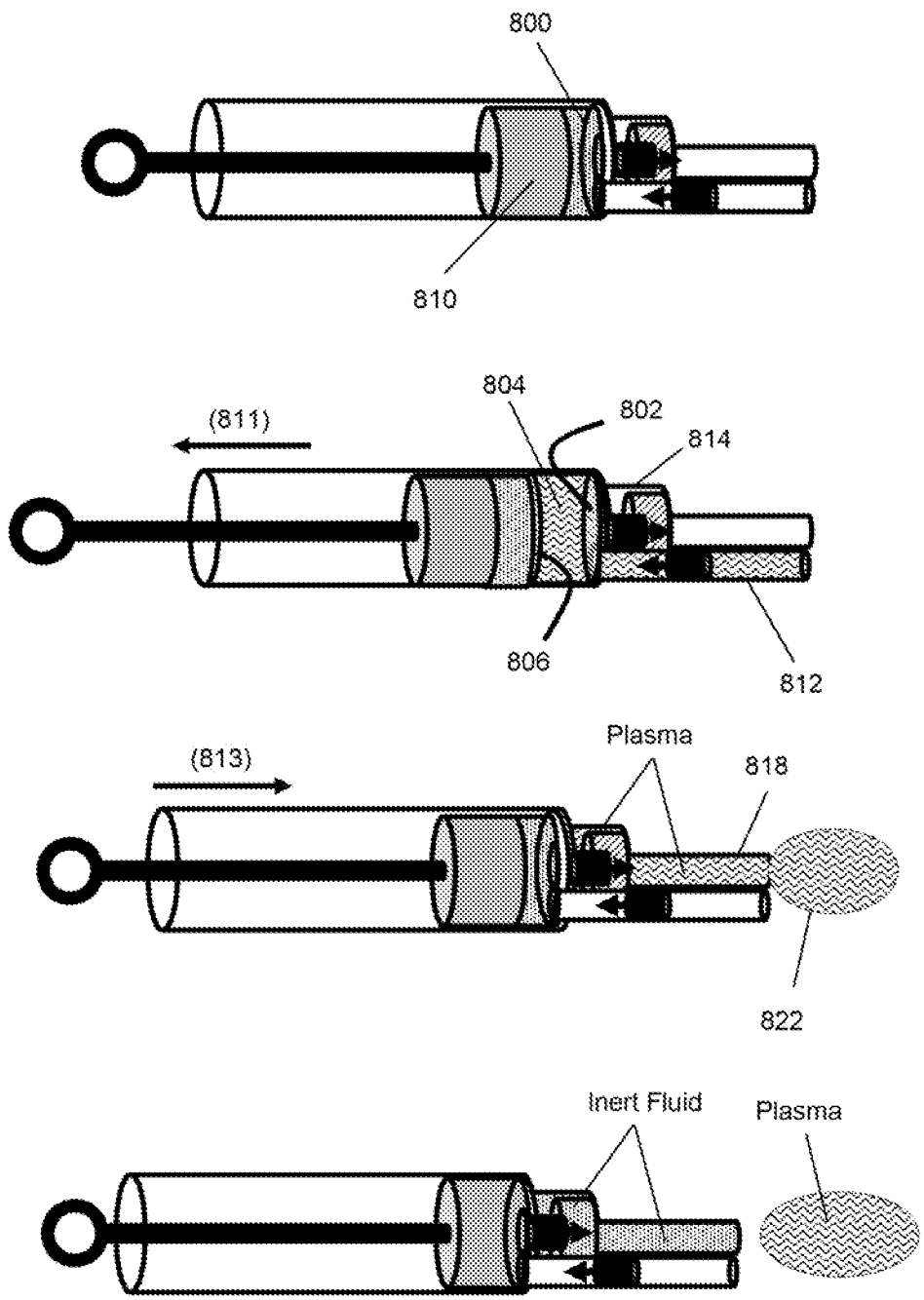
FIG. 8 illustrates an embodiment comprising a component for minimizing dead volume losses.

Some embodiments of the invention provide an element for plasma separation devices to minimize dead volume losses. In FIG. 8, such element is illustrated in the context of a particular plasma separation device and is not meant to be limiting. Reservoir (800) of inert fluid is provided which can be released to follow sample through chambers or passages, thereby displacing and forcing the discharge of sample that would otherwise remain in such chambers or passages. In some embodiments, at least one wall (806) of reservoir (800) is rupturable (to release inert fluid) when contacted with end (802) of sample collection receptacle (804). Upon rupture, plunger (810) continues to move to end (802) of sample collection receptacle (804) forcing inert fluid to displace and push through sample and/or sample components through the outlet of the device. In the illustrated embodiment, plunger (810) is moved back (811) from inlet (812) drawing sample into sample collection receptacle (804). Moving plunger towards (813) inlet (812) and filter chamber (814) moves sample through filter chamber (814) until reservoir (800) at the end of plunger (810) contacts end (802) of sample collection receptacle (804). Further movement of plunger (810) ruptures or otherwise releases a predetermined volume of inert fluid that follows sample into filter chamber (814) and drive sample components residing in filter chamber (814) and/or outlet (818), such as plasma, to be discharged (822) from the device.

We claim:
1. A device for separating plasma from whole blood, the device comprising:
(a) a sample collection receptacle with at least one port, the sample collection receptacle capable of holding a predetermined volume of a sample of whole blood drawn through a port;
(b) a filter chamber having an inlet and an outlet, and containing at least one filter capable of separating plasma from blood cells as sample passes from an inlet side to an outlet side of the at least one filter whenever the filter chamber is placed in fluid communication with a port of the sample collection receptacle; and
(c) a manually driven pump operationally associated with the sample collection receptacle and filter chamber for (i) drawing a predetermined volume of sample into the sample collection receptacle by a first user action and (ii) driving by a spring-drive mechanism or an elastomeric bladder the predetermined volume at a substantially constant linear flow under a pressure not exceeding 2 psi from the sample collection receptacle through the filter chamber and the outlet of the filter chamber by a second user action.
2. The device of claim 1 wherein said port of said sample collection receptacle through which said sample is drawn comprises a one-way valve that prevents fluid from exiting said sample collection receptacle by said port.
3. The device of claim 1 wherein said inlet of said filter chamber comprises a one-way valve that prevents fluid from exiting said filter chamber by said inlet.
4. The device of claim 1 wherein said sample collection receptacle comprises a body and a plunger moveably disposed within the body and forming fluid seals with walls of the body so that by moving the plunger in a first direction a negative pressure is exerted on said sample collection receptacle and by moving the plunger in a second direction a positive pressure is exerted on said sample collection receptacle, and wherein said spring-drive mechanism of said manually driven pump is operationally associated with the plunger and the body so that whenever the spring is in a relaxed state the plunger is disposed in the body to give said sample collection receptacle a first volume, said spring-drive mechanism comprising a releasable catch that permits the spring to be placed in a non-relaxed state by said first user action to give said sample collection reservoir a second volume, thereby causing the plunger to exert a negative pressure on said sample collection receptacle, and to be released from the non-relaxed state by said second user action, thereby returning the spring to return to a relaxed state and causing the plunger to exert a positive pressure not exceeding 2 psi on said sample collection receptacle.

5. The device of claim 4 wherein said first volume is substantially zero.

6. The device of claim 1 wherein said sample collection receptacle comprises said elastomeric bladder, and wherein said elastomeric bladder of said manually driven pump comprises a mechanism for collapsing or releasing the elastomeric bladder such that by said first user action the mechanism releases the elastomeric bladder thereby changing a first volume of said sample collection receptacle to a second volume thereby drawing said sample into said sample collection receptacle, and such that by said second user action the mechanism collapses the elastomeric bladder thereby reducing the second volume and exerting a positive pressure not exceeding 2 psi on said sample.

* * * * *